(12) United States Patent
Erdman

(10) Patent No.: US 7,766,889 B2
(45) Date of Patent: Aug. 3, 2010

(54) ABSORBENT ARTICLE

(75) Inventor: Carol Erdman, West Chester, PA (US)

(73) Assignee: First Quality Retail Services, LLC, Great Neck, NY (US)

( * ) Notice: Subject to any disclaimer, the term of this patent is extended or adjusted under 35 U.S.C. 154(b) by 607 days.

(21) Appl. No.: 10/922,733

(22) Filed: Aug. 20, 2004

(65) Prior Publication Data

US 2006/0041240 A1 Feb. 23, 2006

(51) Int. Cl.
*A61F 13/15* (2006.01)
*A61F 13/20* (2006.01)

(52) U.S. Cl. .......................... 604/385.26; 604/385.25; 604/385.27

(58) Field of Classification Search . 604/385.24–385.3, 604/385.14
See application file for complete search history.

(56) References Cited

U.S. PATENT DOCUMENTS

| | | | | | |
|---|---|---|---|---|---|
| 4,051,853 | A | * | 10/1977 | Egan, Jr. | 604/390 |
| 4,610,678 | A | | 9/1986 | Weisman et al. | 604/368 |
| 4,643,729 | A | * | 2/1987 | Laplanche | 604/389 |
| 4,646,362 | A | | 3/1987 | Heran et al. | 2/400 |
| 4,695,278 | A | * | 9/1987 | Lawson | 604/385.27 |
| 4,704,115 | A | * | 11/1987 | Buell | 604/385.26 |
| 4,704,116 | A | * | 11/1987 | Enloe | 604/385.27 |
| 5,021,051 | A | * | 6/1991 | Hiuke | 604/385.27 |
| 5,098,423 | A | | 3/1992 | Pieniak et al. | 604/385.1 |
| 5,137,537 | A | | 8/1992 | Herron et al. | 8/120 |
| 5,147,345 | A | | 9/1992 | Young et al. | 604/378 |
| 5,281,207 | A | | 1/1994 | Chmielewski et al. | 604/378 |
| 5,314,557 | A | * | 5/1994 | Schwartz et al. | 156/229 |
| 5,496,428 | A | * | 3/1996 | Sageser et al. | 156/73.1 |
| 6,001,471 | A | * | 12/1999 | Bries et al. | 428/343 |
| 6,068,620 | A | | 5/2000 | Chmielewski | 604/378 |
| 6,123,694 | A | | 9/2000 | Pieniak et al. | 604/385.2 |
| 6,248,097 | B1 | * | 6/2001 | Beitz et al. | 604/385.27 |
| 6,468,257 | B1 | * | 10/2002 | Ono et al. | 604/391 |
| 6,547,774 | B2 | * | 4/2003 | Ono et al. | 604/385.29 |
| 6,575,951 | B1 | * | 6/2003 | Ono et al. | 604/385.14 |
| 6,645,338 | B1 | * | 11/2003 | Sangani et al. | 156/289 |
| 6,682,516 | B2 | | 1/2004 | Johnston et al. | 604/385.28 |
| 6,706,029 | B1 | * | 3/2004 | Suzuki et al. | 604/385.28 |
| 2002/0173764 | A1 | * | 11/2002 | Takino et al. | 604/385.28 |
| 2003/0093056 | A1 | * | 5/2003 | Kurata | 604/385.101 |
| 2003/0114827 | A1 | * | 6/2003 | Peterson | 604/385.28 |
| 2005/0113790 | A1 | * | 5/2005 | Suzuki et al. | 604/385.28 |

OTHER PUBLICATIONS

Fig. A: Examiner's markup of Buell's Fig. 2.*
"overlap." Merriam-Webster Online Dictionary. 2009."overlap" Merriam-Webster Online Dictionary. 2009.Merriam-Webster Online. Oct. 19, 2009 <http://www.merriam-webster.com/dictionary/overlap>.*

* cited by examiner

*Primary Examiner*—Melanie J Hand
(74) *Attorney, Agent, or Firm*—Amster, Rothstein & Ebenstein LLP

(57) ABSTRACT

An absorbent article is provided including a backsheet, a topsheet and an absorbent core disposed therebetween. The diaper includes large rectangular fasteners that stretch in only one direction. At least one longitudinally extending, elasticized inner leg gather is disposed with the topsheet. The inner leg gather includes at least one elastic member for distributing elastic contractile forces. The inner leg gather is joined to the topsheet along a front tackdown zone and a back tackdown zone. The elastic members and tackdown zones extend in a manner sufficient to provide enhanced fit, functionality and waste containment. The unidirectional stretch fasteners and leg gathers are sized in relationship to each other to enable a complete encircling of each leg to form a better leg gasket for waste containment and fit.

15 Claims, 8 Drawing Sheets

ABSORBENT ARTICLE

BACKGROUND

1. Technical Field

The present disclosure generally relates to disposable absorbent articles, and more particularly, to disposable absorbent articles with improved fasteners and leg gathers.

2. Background of the Related Art

Absorbent articles such as, for example, disposable diapers, adult incontinent pads, sanitary napkins, pantiliners, incontinent garments, etc. are generally worn, in cooperation with garments and disposed against a body surface by infants or adult incontinent individuals. The absorbent article is employed to collect and absorb body fluid discharge, such as, for example, blood, menses, urine, aqueous body fluids, mucus and cellular debris. For example, the absorbent article may be disposed between the legs of an individual adjacent a crotch area. The absorbent article is positioned with a garment and drawn into engagement with a body surface of the crotch area to collect fluid discharge.

As is known, absorbent articles typically include a fluid permeable coverstock for engaging the body surface, a fluid impermeable backsheet and an absorbent core supported therebetween. The backsheet serves as a moisture barrier to prevent fluid leakage to the garment. The absorbent core usually includes a liquid retention material that faces the body surface. The absorbent core can include, for example, loosely formed cellulosic fibers, such as wood pulp, for acquiring and storing fluid discharge.

Although the absorbent core typically is capable of absorbing and storing a relatively large quantity of body exudates, the rate at which body exudates are expelled, as well as the quantity of body exudates expelled, often can overwhelm the absorbent action of the absorbent core, resulting in unabsorbed body waste and fluids between the body of the wearer and the surface of the topsheet. Accordingly, many absorbent garments include standing leg gathers, inner leg gathers ("ILG's") and other types of leg gathers to form leg-encircling barriers to the leakage of unabsorbed body exudates from the absorbent garment. The containment capabilities of these standing leg gathers typically are enhanced by including elastic elements along a portion of the length of the standing leg gather to provide a contractile force that further constricts the standing leg gather against the leg of the wearer, thereby reducing the ability of unabsorbed exudates to escape from between the leg of the wearer and the edge of the standing leg gather in contact with the leg of the wearer. In effect, the standing leg gather is intended to form a "gasket" between the body of the wearer and the absorbent garment, thereby inhibiting the leakage of body exudates. See, for example, U.S. Pat. Nos. 6,682,516 and 6,123,694, which are hereby incorporated by reference in their entirety.

Some of these leg gathers, however, suffer from performance drawbacks including poor fit with the body surface. These drawbacks can disadvantageously result in leakage and discomfort to the wearer.

Despite these and other efforts by absorbent garment manufacturers and others to provide suitable leg gathers for absorbent garments, there is still a need to provide a more functional, comfortable, and better fitting leg gather. These are just a few of the objectives that the preferred embodiments seek to address. Hence, it would be desirable to provide an absorbent article including leg gathers that improve fit, functionality as well as better waste containment. It would also be desirable if the absorbent article and its constituent parts are easily and more efficiently manufactured.

In addition, fastening of the absorbent articles with an individual requires the use of fasteners or ear members and closure tabs that extend laterally from the body of the absorbent article. In addition, the closure tabs typically include mechanical closure material, for example, hook and/or loop material, adhesive tape or the like. For example, in typical diaper-type garments, the garment is affixed to a wearer by attaching one or more of the closure tabs that extend across the wearer's hips to hold the back and front halves of the garment to one another.

Some of these absorbent articles, however, suffer from performance drawbacks including poor fit with the body surface. These drawbacks can disadvantageously result in leakage and discomfort to the wearer. Attempts to overcome these drawbacks include providing fasteners having mechanical closure systems that employ an elastic portion for customizing the fit of an absorbent article to a particular individual. However, these fasteners can be stretched in multiple directions along the body of an individual. This can disadvantageously result in an improper fit and alignment, leakage and discomfort to the wearer.

It would therefore be desirable to overcome the disadvantages and drawbacks of the prior art by providing an absorbent article including fasteners that cooperate with leg gathers to improve waste containment and fit of the absorbent article to an individual. It would be desirable if the absorbent article and its constituent parts are easily and efficiently manufactured.

One typical absorbent article 70 is shown in FIGS. 1 and 2, and includes a top sheet 72, a backsheet 74 and an absorbent core 76 therebetween, and leg gathers 80 (FIG. 2). Fasteners 78 are extensible in both the lateral 102 and longitudinal 100 directions (FIG. 2). There is concern that in use such fastener exerts opposing forces, which may pull the diaper downward, causing poor fit (FIG. 1). In addition, the relatively small fastener 78 is the only means for holding diaper 70 up (in place) and for providing coverage on the sides. Thus, fastener 78 and leg gather 80 may encircle the wearer's leg less than completely, resulting in poorer waste containment and fit. This is particularly so when the diaper's side panels 82, 84 shift in response to the movement of an active infant wearer. Because fastener 78 is small, the overall width of diaper 70 is made wide particularly along side panels 82, 84 in order to provide coverage. Accordingly, more material is required to manufacture diaper 70 along with increased production costs.

SUMMARY

Accordingly, an absorbent article is disclosed that includes an absorbent article including leg gathers and fasteners that cooperate to improve waste containment. The absorbent article and its constituent parts are easily and efficiently manufactured.

Objects and advantages of the present disclosure are set forth in part herein and in part will be obvious therefrom, or may be learned by practice of the present disclosure that is realized and attained by the instrumentalities and combinations pointed out in the appended claims for the devices and methods of the present disclosure consisting of its constituent parts, constructions, arrangements, combinations, steps and improvements herein shown and described.

In one particular embodiment, the absorbent article, which may be a diaper, includes a backsheet, a topsheet, and an absorbent core disposed therebetween. The diaper extends from a first end to a second end along a longitudinal centerline of the diaper. At least one longitudinally extending, elasticized inner leg gather is disposed with the topsheet. This inner leg gather includes at least one elastic member for distributing elastic contractile forces. This elastic member extends between 75 and 95 percent of a length of the diaper. A lengthwise portion of the elastic member forms gathered sections along the inner leg gather.

The inner leg gather is joined to the topsheet along a front tackdown zone and a back tackdown zone. These front and back tackdown zones have a combined length of 10 to 25 percent of the length of the diaper. The front tackdown zone extends from an edge of the first end and the back tackdown zone extends from an edge of the second end. These front and back tackdown zones do not include the above-mentioned gathered sections.

In another embodiment, the diaper of the present disclosure includes an inner leg gather joined to the topsheet along at least one tackdown portion. The inner leg gather includes at least one elastic member for distributing elastic contractile forces. The ratio of a length of the elastic member to a length of the tackdown portion is between 2.5 to 1 and 4.5 to 1.

In another embodiment, a fastener of the present disclosure is adapted for use with an absorbent article, and includes at least one non-extensible portion. The fastener also includes an extensible portion configured to extend in a single lateral direction such that the fastener extends distally from the absorbent article. The non-extensible portion is a closure tab that includes hook elements configured for attachment with the absorbent article. The extensible portion is situated between the absorbent article and the non-extensible portion, and the non-extensible portion is substantially centered along a distal edge of the extensible portion. The extensible portion has a greater surface area relative to the non-extensible portion. In use, the fastener provides lateral forces across a wearer's waist and upper leg regions.

In another embodiment, an absorbent article of the present disclosure includes a pair of fasteners connected to a first end thereof and configured to extend in a single direction relative to the first end. The fasteners exert a force around a wearer's waist and outer leg regions, and the force is exerted in a single lateral cross-direction. The first end is configured for engagement with a rear portion of a subject and a second end is configured for engagement with a front portion of the subject. The fastener includes an extensible portion connected to the first end and a non-extensible closure tab connected to the extensible portion. The extensible portion has a greater surface area relative to the non-extensible portion. The non-extensible portion includes mechanical closure elements configured for attachment with the absorbent article. The absorbent article extends from the first end to the second end along a longitudinal axis thereof, and the single direction extends along an axis transverse to the longitudinal axis of the absorbent article.

In another embodiment, the diaper of the present disclosure extends from a rear end to a front end along a longitudinal axis of the diaper, and includes a pair of fasteners adhesively bonded to opposite sides of the rear end. The fasteners are elastic in a single direction in a transverse axis relative to the longitudinal axis. The fasteners provide a transverse securing force around the subject's waist.

In another embodiment, the diaper of the present disclosure includes a rear end having a fastener attachment area. The fastener attachment area includes a fastener attached thereto. The length of the fastener is between 45-70% of the length of the fastener attachment area.

In another embodiment, the diaper of the present disclosure includes a fastener attached to the rear end of the diaper. The length of the fastener is between 8-18% of the length of the diaper.

In another embodiment, the absorbent article of the present disclosure has a first end including a fastener attachment area for attaching a fastener thereto. The length of the fastener is between 45-70% of the length of the fastener attachment area. The fastener includes an extensible portion configured to extend in a single lateral direction such that the fastener extends distally from the absorbent article. The fastener is configured to engage an upper portion of a leg of a subject to facilitate containment about the upper portion of the leg of the subject. At least one longitudinally extending, elasticized inner leg gather is disposed with a topsheet of the absorbent article. The leg gather engages the leg to facilitate containment about a lower portion of the leg of the subject.

BRIEF DESCRIPTION OF THE DRAWINGS

The objects and features of the present disclosure are set forth with particularity in the appended claims. The present disclosure, as to its organization and manner of operation, together with further objectives and advantages may be understood by reference to the following description, taken in connection with the accompanying drawings, in which:

DETAILED DESCRIPTION OF EXEMPLARY EMBODIMENTS

Figure 1:
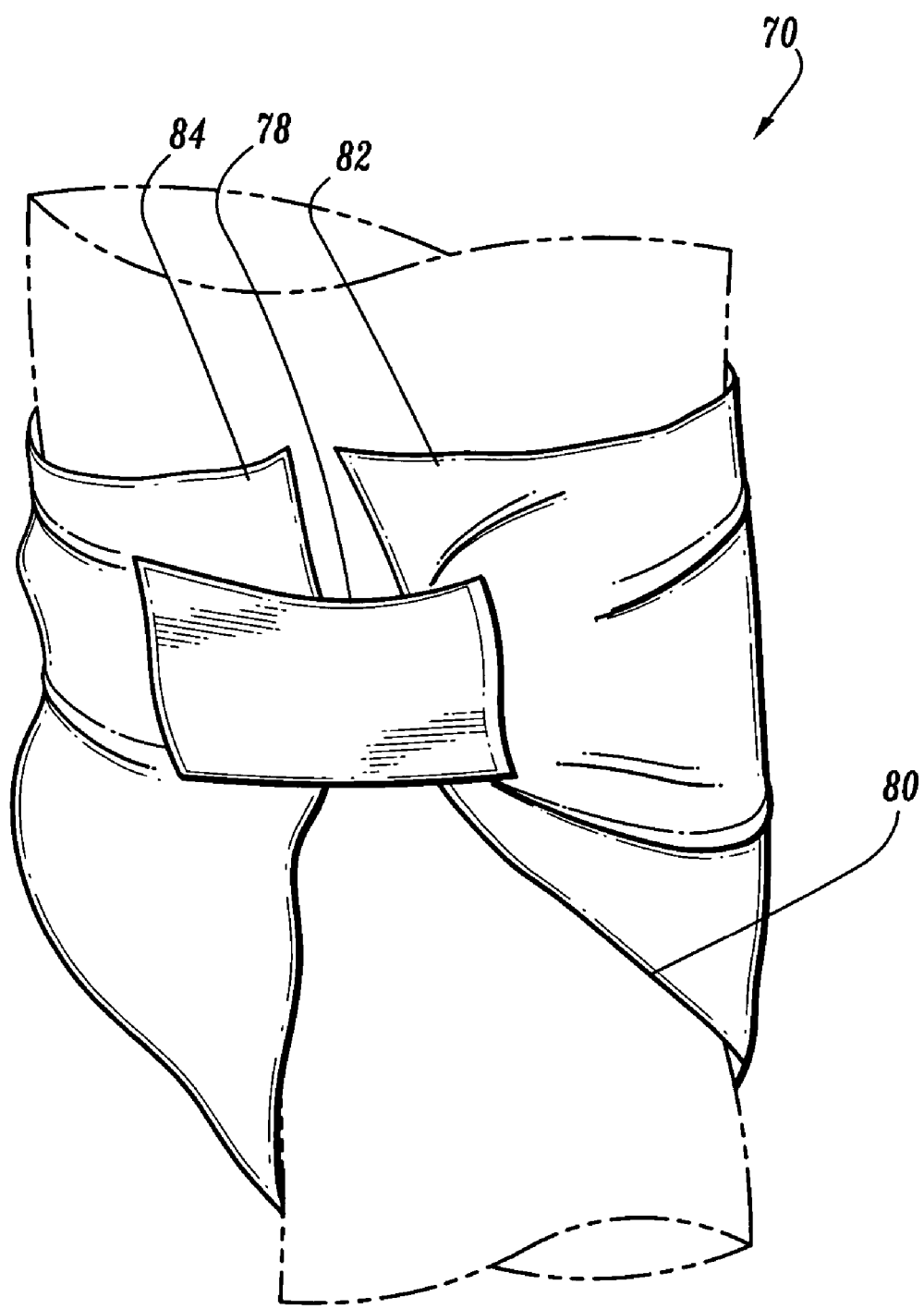
FIG. 1 is a perspective view of an absorbent article according to the prior art.

The exemplary embodiments of the absorbent article and methods of use disclosed are discussed in terms of fluid absorbent articles, and more particularly, in terms of an absorbent article including fasteners and inner leg gathers that cooperate to improve waste containment and fit. The presently disclosed absorbent article avoids leakage and overflow of fluid discharge, such as, for example, blood, menses, urine, aqueous body fluids, mucus and cellular debris. It is contemplated that the absorbent article may be employed with, for example, disposable diapers, adult incontinent pads, feminine pads, sanitary napkins, or incontinent garments.

In the discussion that follows, the term "body-facing surface" refers to a portion of a structure that is oriented towards a body surface, and the "garment-facing surface" refers to a portion of the structure that is oriented towards a garment and is typically opposing the body-facing surface and may be referred to as such. As used herein, the term "body surface" refers to a portion of an individual's body that the absorbent article is disposed with for collecting and absorbing fluid discharge from the individual. As used herein, the term "absorbent article," "absorbent garment" or "garment" refers to garments that absorb and contain exudates, and more specifically, refers to garments that are placed against or in proximity to the body of the wearer to absorb and contain the various exudates discharged from the body.

A non-exhaustive list of examples of absorbent garments includes diapers, diaper covers, disposable diapers, training pants, feminine hygiene products and adult incontinence products. The term garment includes all variations of absorbent garments, including disposable absorbent garments that are intended to be discarded or partially discarded after a single use (i.e., they are not intended to be laundered or otherwise restored or reused) and unitary disposable absorbent garments that have essentially a single structure (i.e., do not require separate manipulative parts such as a diaper cover and insert). As used herein, the term "diaper" refers to an absorbent garment generally worn by infants and incontinent persons about the lower torso.

The claims are intended to cover all of the foregoing classes of absorbent garments, without limitation, whether disposable, unitary or otherwise. These classifications are used interchangeably throughout the specification, but are not intended to limit the claimed invention. The invention will be understood to encompass, without limitation, all classes of absorbent garments, including those described above.

Absorbent garments and diapers may have a number of different constructions. In each of these constructions it is generally the case that an absorbent core is disposed between a liquid pervious, body-facing topsheet, and a liquid impervious, exterior facing backsheet. In some cases, one or both of the topsheet and backsheet may be shaped to form a pant-like garment. In other cases, the topsheet, backsheet and absorbent core may be formed as a discrete assembly that is placed on a main chassis layer and the chassis layer is shaped to form a pant-like garment. The garment may be provided to the consumer in the fully assembled pant-like shape, or may be partially pant-like and require the consumer to take the final steps necessary to form the final pant-like shape, such as by fastening one or more fastener tabs.

In the case of some diapers and most adult incontinent products, the garment often is provided fully formed with factory-made side seams and the garment is donned by pulling it up the wearer's legs. In the case of most diapers, wherein, for example, a baby lies on his or her back, a caregiver usually places the diaper between the baby's legs, pulls the front end of the diaper up between the legs and then attaches one or more closure tabs to the rear end of the diaper, thereby forming a pant-like structure. For clarity, the present invention is described herein only with reference to a diaper-type garment in which the topsheet, backsheet and absorbent core are assembled into a structure that forms a pant-like garment when secured on a wearer using fastening devices, although the invention may be used with any other type of absorbent garment that may benefit from the use or addition of fastener tabs.

The following discussion includes a description of the absorbent article in accordance with the present disclosure. Reference will now be made in detail to the exemplary embodiments of the disclosure, which are illustrated in the accompanying Figures.

Turning now to the Figures, wherein like components are designated by like reference numerals throughout the several views. Referring to FIGS. 3-9, there is illustrated an absorbent article, constructed in accordance with the principles of the present disclosure, such as, for example diaper 10. An improved diaper 10 is provided, as compared with an example of the prior art shown in FIGS. 1 and 2. In FIG. 3, diaper 10 is shown in a relaxed condition with the effects of the elastics removed for purposes of clarity in the description. The diaper 10 chassis generally has an hourglass shape. The chassis generally can be defined in terms of a front waist region 22, a back waist region 24, and a crotch region 26. Those skilled in the art will recognize that "front" and "back" are relative terms, and these regions may be transposed without departing from the scope of the present invention. Alternatively, the diaper chassis can be configured in a generally rectangular shape or in a "T" shape. The diaper preferably comprises a topsheet 2, a backsheet 4, which may be either a different size than the topsheet 2 or may be substantially coterminous with the topsheet 2, and an absorbent core 6 disposed between at least a portion of the topsheet 2 and backsheet 4. Throughout this description, the terms "topsheet" and "backsheet" denote the relationship of these materials or layers with respect to the absorbent core 6. It is understood that additional layers may be present between or beyond the absorbent core 6 and the topsheet 2 and backsheet 4, and that additional layers and other materials may be present on the side opposite the absorbent core 6 from either the topsheet 2 or the backsheet 4. A pair of leg openings 28a, 28b extend along at least a portion of the crotch region 26 and one or more pairs of leg elastics 8 (three pairs are shown in FIG. 3) may be disposed to extend adjacent to leg openings 28a, 28b. Of course, in other embodiments, the number of leg elastics 8 may be increased, decreased or omitted altogether.

The diaper 10 generally has a longitudinal direction 100 that extends generally parallel to the front-to-back axis of a wearer, and a lateral direction 102 that extends generally parallel to the side-to-side axis of a wearer. The diaper 10 generally is symmetrical about a longitudinal centerline 60, but also may have asymmetrical components or shapes. The terms "inboard" or "proximal," and "outboard" or "distal," as used herein, refer to positions generally along the lateral direction 102, with "inboard" locations being located closer to the longitudinal centerline 60 than "outboard" locations. "Outward" and "inward" mean in an outboard or inboard direction, respectively.

The diaper may further include a waste containment system in the form of waste containment flaps 12 (also known as inner leg gathers ("ILG's"), unitary leg gathers or standing leg gathers). Waste containment flaps 12 preferably extend from the front waist region 22 to the back waist region 24 along opposite sides of the longitudinal center line 60 of the diaper 10, or alternatively only along a portion thereof. The front waist region 22 and rear waist region 24 preferably include side panels, or ear portions 38, 46, extending outward from the leg openings 28a, 28b to provide the garment 10 with an hourglass shape.

A variety of backsheet and topsheet constructions and materials are available and known in the art, and the invention is not intended to be limited to any specific materials or constructions of these components. The backsheet 4 may be made from any suitable pliable liquid-impervious material known in the art. Typical backsheet materials include films of polyethylene, polypropylene, polyester, nylon, and polyvinyl chloride and blends of these materials. For example, the backsheet can be comprised of a pigmented polyethylene film having a thickness in the range of 0.02-0.04 mm. The moisture-pervious topsheet 2 can be made of any suitable relatively liquid-pervious material known in the art that permits passage of liquid therethrough. Non-woven topsheet materials are exemplary because such materials readily allow the passage of liquids to the underlying absorbent core 6. Examples of suitable topsheet materials include non-woven spunbond or carded webs of polypropylene, polyethylene, nylon, polyester and blends of these materials.

The backsheet 4 and the topsheet 2 preferably are "associated" with one another. The term "associated" encompasses configurations whereby the topsheet 2 is directly joined to the backsheet 4 by affixing the topsheet 2 directly to the backsheet 4, and configurations whereby the topsheet 2 is indirectly joined to the backsheet 4 by affixing the topsheet 2 to intermediate members which in turn are affixed to the backsheet 4. While the backsheet 4 and topsheet 2 in the preferred embodiment have substantially the same dimensions, they may also have different dimensions.

In addition, the backsheet 4 may be covered with a fibrous, non-woven fabric layer such as is disclosed, for example, in U.S. Pat. No. 4,646,362, which is incorporated herein by reference in its entirety and in a manner consistent with the present invention. Materials for such a fibrous outer liner include a spun-bonded non-woven web of synthetic fibers such as polypropylene, polyethylene or polyester fibers; a non-woven web of cellulosic fibers, textile fibers such as rayon fibers, cotton and the like, or a blend of cellulosic and textile fibers; a spun-bonded non-woven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers.

The backsheet 4 may comprise multiple panels, such as three panels wherein a central poly backsheet panel is positioned adjacent the absorbent core while outboard non-woven breathable side backsheet panels are attached to the side edges of the central poly backsheet panel. The backsheet may also be formed from microporous poly coverstock for added breathability. In other embodiments, the backsheet may be a laminate of several sheets. The backsheet may further be treated to render it hydrophilic or hydrophobic, and may have one or more visual indicators associated with it, such as labels indicating the front or back of the diaper or other characters or colorations. The present invention is not limited to any particular backsheet 4 material or construction.

The topsheet 2 may be formed from one or more panels of material and may comprise a laminated sheet construction. In the embodiment of FIGS. 3 and 4, the topsheet comprises one panel across the entire width of the diaper and preferably is formed from a liquid-pervious material that is either hydrophobic or hydrophilic. Topsheet 2 may be made from any number of materials, including synthetic fibers (e.g., polypropylene or polyester fibers), natural fibers (e.g., wood or cellulose), apertured plastic films, reticulated foams and porous foams to name a few. One preferred material for topsheet 2 is a cover stock of single ply non-woven material which may be made of carded fibers, either adhesively or thermally bonded, perforated plastic film, spunbonded fibers, or water entangled fibers, which generally weigh from 0.3-0.7 oz./yd$^2$ and have appropriate and effective machine direction and cross-machine direction strength suitable for use as a baby diaper cover stock material, as are known in the art. Topsheet 2 preferably extends from substantially the front waist region 22 to the back waist region 24 or a portion thereof, and includes a surfactant (at least along the core area) to aid in the passage of exudates to the core 6.

The waste containment flaps 12 may be formed from separate elasticized strips of material that are associated with the topsheet, backsheet or both, or otherwise integrated into the garment. In another preferred embodiment, the topsheet 2 and backsheet 4 have similar dimensions or different dimensions, but in either case, the waste containment flaps 12 are attached to the topsheet 2 or to some intermediate element which in turn is attached to the topsheet 2. The waste containment flaps 12 may be treated with a suitable surfactant to modify their hydrophobicity/hydrophilicity or imbued with skin wellness products as desired. Each waste containment flap 12 preferably includes a portion that folds over onto itself to form an enclosure. One or more elastic members 14 may be secured in the enclosure in a stretched condition. As has been known at least as long as the disclosure of U.S. Pat. No. 4,695,278 to Lawson, et al., when the flap elastic 14 attempts to assume the relaxed, unstretched condition, the waste containment flaps 12 rise above the surface of topsheet 2. Various other configurations of topsheets 2 and waste containment systems, such as flaps 12, are known in the art, and the present invention is not intended to be limited to any particular design for these components.

Each leg opening 28*a*, 28*b* may be provided with a leg elastic containment system 8, sometimes referred to as conventional leg gathers. In an illustrative embodiment, three strands of elastic threads are positioned to extend adjacent each leg openings 28*a*, 28*b* between the topsheet 2 and the backsheet 4. The selection of appropriate elastics and the construction of leg elastic containment systems are known in the art. For example, the leg elastics 8 may be ultrasonically bonded, heat/pressure sealed using a variety of bonding patterns, or glued to the diaper 10. Leg gathers 12 may be formed with or as separate members from topsheet 2.

Various commercially available materials may be used for the leg elastics 8 and elastic members 14, such as natural rubber, butyl rubber or other synthetic rubber, urethane, elastomeric materials such as spandex, which is marketed under various names, including LYCRA® (DuPont), GLOSPAN™ (Globe) and SYSTEM 7000™ (Fulflex), and so on. The present invention is not limited to any particular elastic material or to any particular shape, size or number of elastics.

The underlying structure beneath the topsheet 2 may include, depending on the absorbent garment construction, various combinations of elements, but in each embodiment, it is contemplated that the absorbent garment preferably will include an absorbent core 6. Although the absorbent core 6 depicted in FIG. 3 has a substantially rectangular shape as viewed in the plan view, other shapes may be used, such as a "T" shape or an hourglass shape. The absorbent core 6 may extend into either or both of the front and back waist regions 24, 22. The shape and construction of the absorbent core 6 may be selected to provide the greatest absorbency in target areas where body fluids are most likely to strike the diaper 10, which is often referred to as zoned absorbency. The absorbent core 6 may also comprise a number of layers of similar or different construction. The absorbent core may be associated with the topsheet 2, backsheet 4, or any other suitable part of the garment 10 by any method known in the art, in order to fix the absorbent core 6 in place.

Generally, in an illustrative embodiment, the absorbent core 6 comprises particles of superabsorbent material (SAP) distributed within a fibrous structure. Additional fibrous or particulate additives may be disposed within the absorbent core 6 to add to the core's strength and SAP efficiency or to otherwise enhance the performance of the garment. The absorbent core 6 may be partially or wholly surrounded by additional layers (not shown) added to provide further benefits. The additional layer or layers may comprise any useful layer known in the art or developed hereafter, such as a fluid acquisition layer, a distribution layer, an additional fibrous layer optionally containing superabsorbent particles (SAP), a wicking layer, a storage layer, or combinations and fragments of these layers. Such layers may be provided to assist with transferring fluids to the absorbent core 6, handling fluid surges, preventing rewet, containing absorbent material, improving core stability, or for other purposes.

The absorbent core 6 may be made from any absorbent material or materials, or combinations of such materials, known in the art or hereafter discovered. In one embodiment of the invention, the absorbent core 6 comprises wood fibers or other fibers such as chemical wood pulp, fibrous absorbent gelling material, or any other suitable liquid absorbing material, such as commercially available fluff pulp or fluffed bleached kraft softwood pulp or fibrous absorbent gelling material. In another embodiment of the invention, the absorbent core 6 comprises a combination of a porous fibrous web and superabsorbent particles. Absorbent cores are known in the art and exemplary cores are disclosed, for example, in U.S. Pat. No. 5,281,207 issued to Chmielewski et al., U.S. Pat. No. 4,610,678 issued to Weisman et. al., U.S. Pat. No. 5,137,537 issued to Herron et. al., U.S. Pat. No. 5,147,345 issued to Young et. al., and U.S. Pat. No. 6,068,620 issued to Chmielewski, all of which are incorporated herein by reference in their entirety, and in a manner consistent with the present invention.

Preferably, the absorbent core is thin in order to improve the comfort and appearance of a garment. The importance of thin, comfortable garments is disclosed, for example, in U.S. Pat. No. 5,098,423 to Pieniak et al., which is incorporated herein by reference in its entirety and in a manner consistent with the present invention.

Referring to FIG. 3, diaper 10 is fastened onto a wearer by using one or more, and preferably two, fastener tabs or fasteners 32. Fasteners 32 preferably are affixed to the chassis of the diaper 10 to extend laterally outward (i.e., in the lateral direction 102) from a waist region 22, 24 of the garment. The fastener tabs 32 preferably are positioned to extend outward from the ear portions 46 of the rear waist region 24, but the fastener tabs 32 may also be attached to extend outward from the front waist region 22, or from both waist regions. The fastener tabs 32 may extend from one, but preferably both, lateral sides of the diaper 10. The fasteners 32 may be attached to any part of the diaper chassis, such as topsheet 2, backsheet 4, outer cover or other layer of the diaper. The fastener tabs 32 may also be attached to either side of the diaper's chassis, to multiple layers of the chassis, or may be sandwiched between the various sheets comprising the chassis of the diaper 10. For example, fastener 32 may be positioned between topsheet 2 and backsheet 4. In this case, one side of fastener 32 is attached to the inside of backsheet 4, and topsheet 2 is glued to the other side of fastener 32. Variations on the number, location, and attachment configuration of the fasteners 32 will be apparent to those skilled in the art based on the teachings herein, and all such variations are within the scope of the present invention.

Each of a pair of closure tabs 33 is attached along distal portion 23 of fastener 32 by adhesive bonding. It is contemplated herein that fasteners 32 and closure tabs 33 may be formed with materials that are elastic, non-elastic or a combination thereof and may be attached to the diaper 10 or each other by adhesive, ultrasonic, thermal bonding or the like. Closure tab 33 may include any hook-and-loop type material, adhesive, or other type of mechanical closure material 34 that is capable of holding diaper 10 on a wearer. Closure tab 33 operates by engaging with or adhering to a corresponding surface, landing zone or object (not shown) located on the opposite end of the diaper 10, preferably front end 20.

Figure 5:
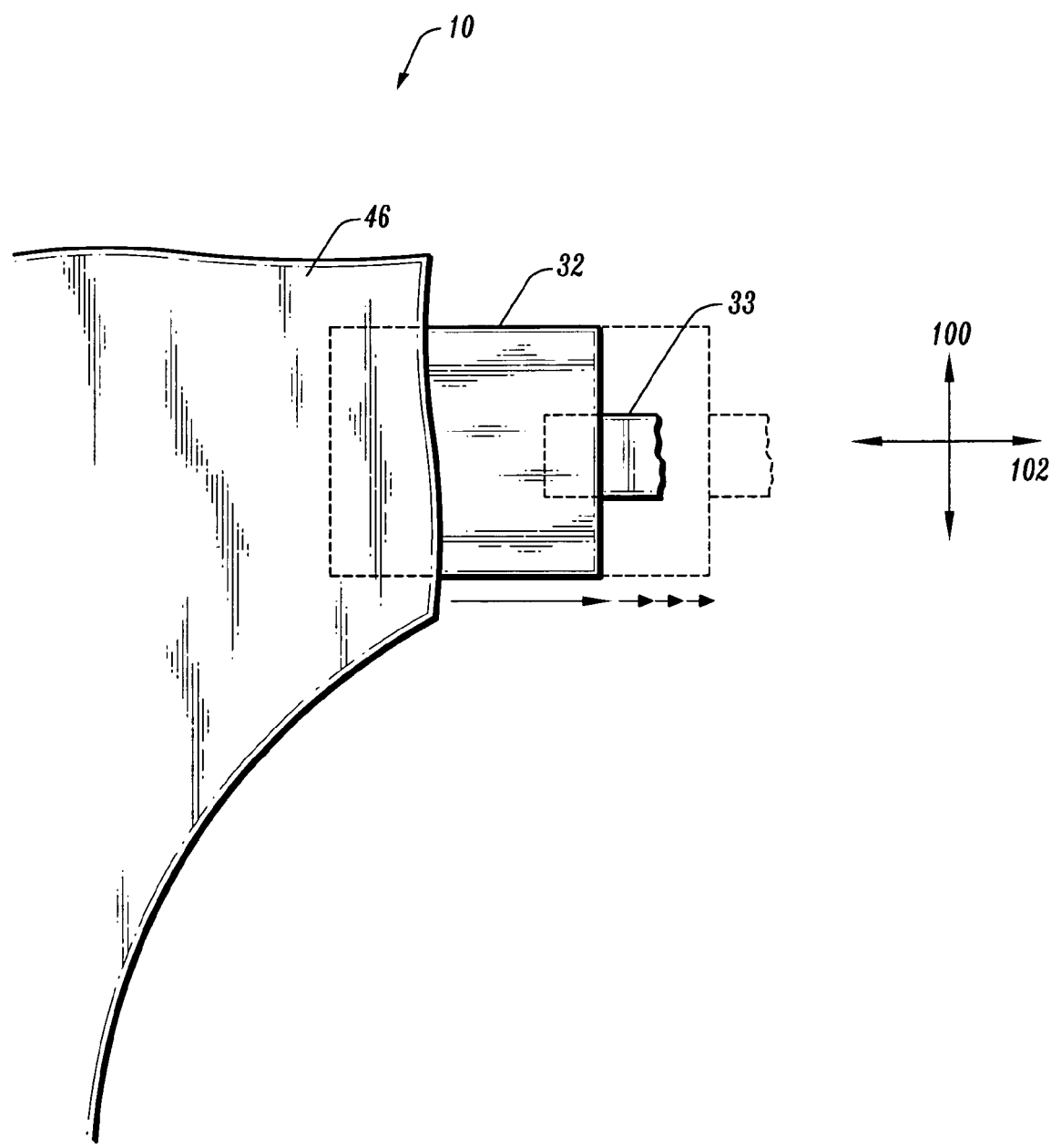
FIG. 5 is a partial plan view of the absorbent article according to the present disclosure.

With reference to FIG. 5, diaper 10 of the present invention includes a large rectangular fastener 32 that only stretches in the lateral direction 102, with a smaller non-stretch closure tab 33. One advantage of this construction is that uni-directional fastener 32 only exerts force around the waist of the wearer. In contrast, a prior art multi-directional fastener exerts opposing forces which pull the diaper downward, causing poor fit. In addition, fastener 32 has a "zoned" stretch property, in that, only certain lengthwise portions or zones thereof will extend or stretch during use. Referring to FIG. 3, fastener 32 includes center, distal, and proximal sections. Center section 27 is stretchable in lateral direction 102. Distal section 23 is generally not stretchable. Proximal section 25 is generally not stretchable and is attached to the diaper chassis. Rectangular fastener 32 may have at least one side equal to or greater than 50 mm, or may square shaped with sides of equal length.

Figure 6:
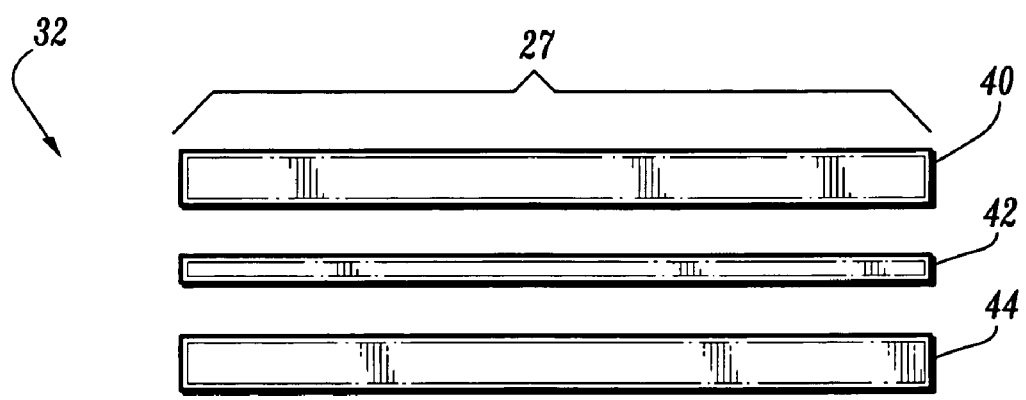
FIG. 6 is a partial side view of the absorbent article according to the present disclosure.

FIG. 6 illustrates an exploded partial side view of fastener 32. As can be seen, stretchable zone 27 may comprise an elastic composite or laminate having an extensible layer 42, and at least one non-woven layer 40 adjacent thereto. In the illustrative embodiments, stretchable zone 27 has extensible layer 42 intermediate or sandwiched between a first non-woven layer 40 and a second non-woven layer 44. Non-extensible proximal and distal portions 23, 25 of FIG. 3 include layers 40, 42, 44 and also include a layer of non-stretch or non-elastic film (not shown).

Extensible layer 42 may be, for example, a urethane based elastic or stretch film, such as EXTRAFLEX® available from Tredegar Film Products of Richmond, Va. However, elastic layer 42 may also be another type of elastic film, a multidirectional elastic aggregate such as elastic webbing, netting, or scrim elastic, foam, strands or bands of suitable elastic materials, such as natural or synthetic rubber, spandex, LYCRA® and elastic polymers. Other suitable elastics will be apparent to those skilled in the art in light of the present disclosure.

Non-woven layers 40, 44 may be, for example, spun-bonded polypropylene, polyethylene, or other non-woven material that encases elastic layer 42, protects the elastic layer 42, protects the wearer from uncomfortable exposure to the elastic layer 42 or provides other benefits. Other uses for the non-woven layers 40, 44 will be apparent to those skilled in the art based on the present disclosure.

The bonding between layers 40, 42, 44 of fastener 32 may be accomplished using joining methods known in the art, such as, for example, compression bonds, heat bonds, ultrasonic bonds, adhesives and the like, or combinations of different bonding methods. The construction of such elastic laminates is known in the art, and a skilled artisan will be able to provide a suitable elastic laminate or other elastic design for fastener 32 without undue experimentation.

Figure 2:
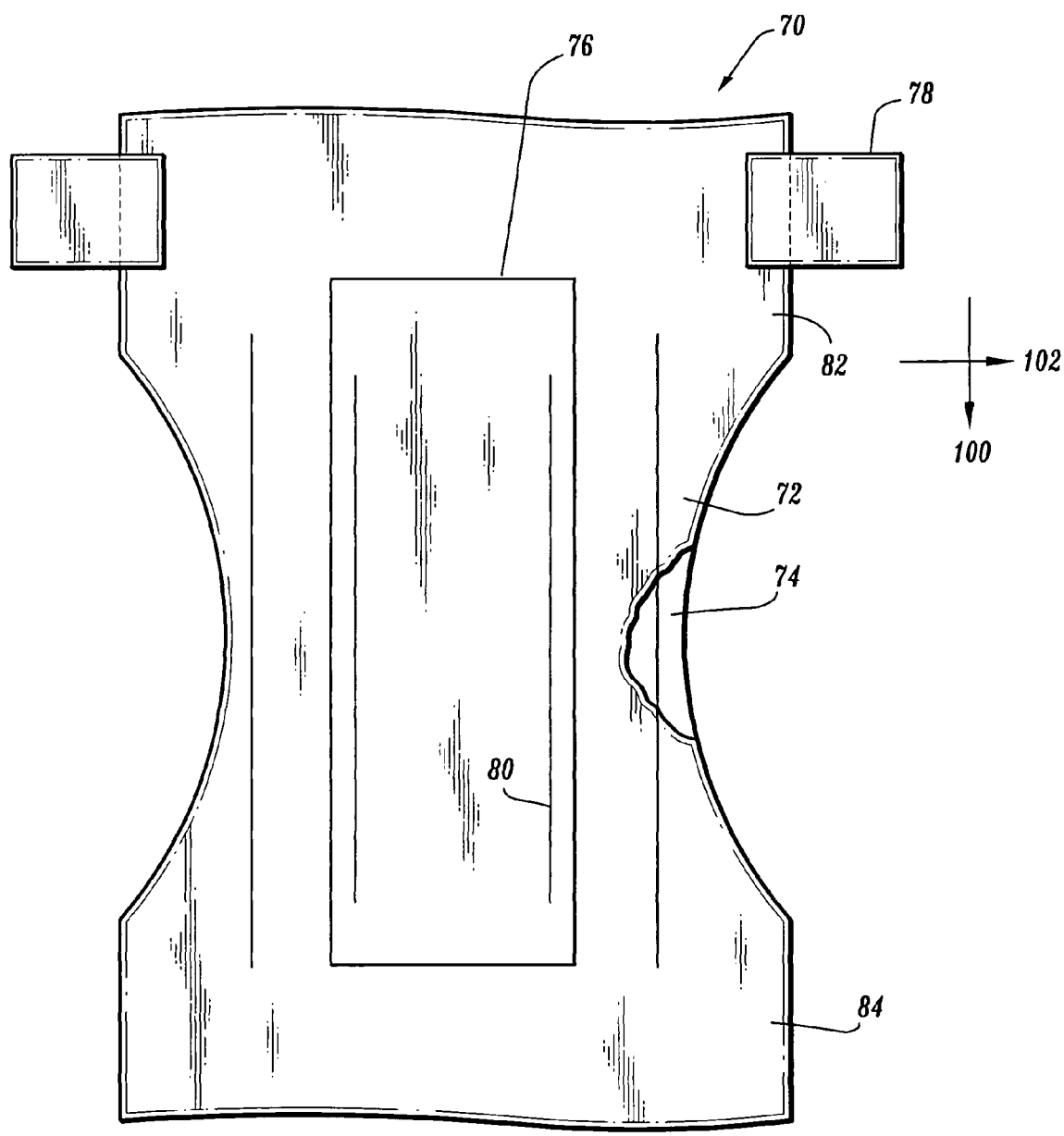
FIG. 2 is a plan view of an absorbent article according to the prior art.
Figure 3:
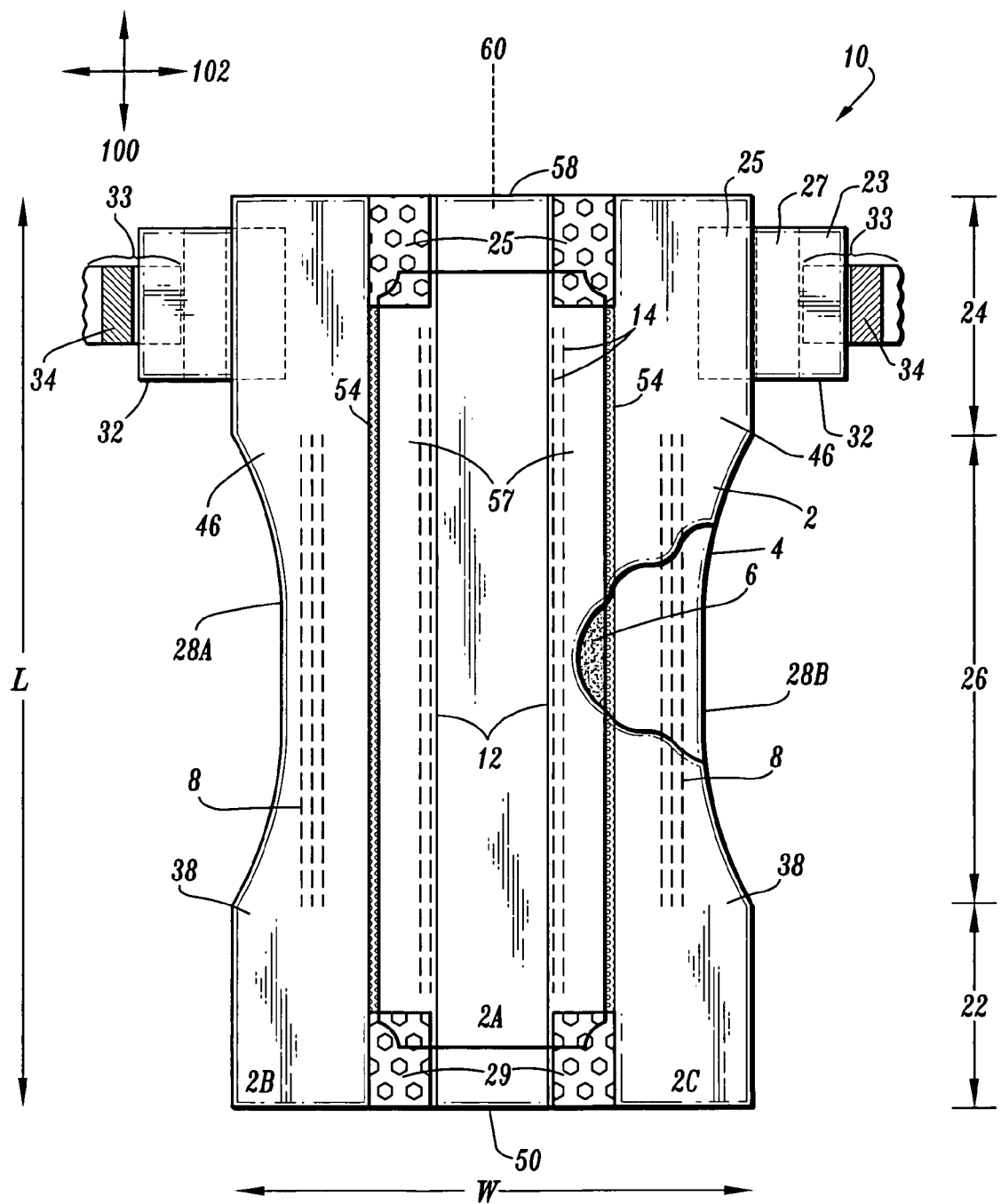
FIG. 3 is a plan view of an absorbent article according to the present disclosure.
Figure 4:
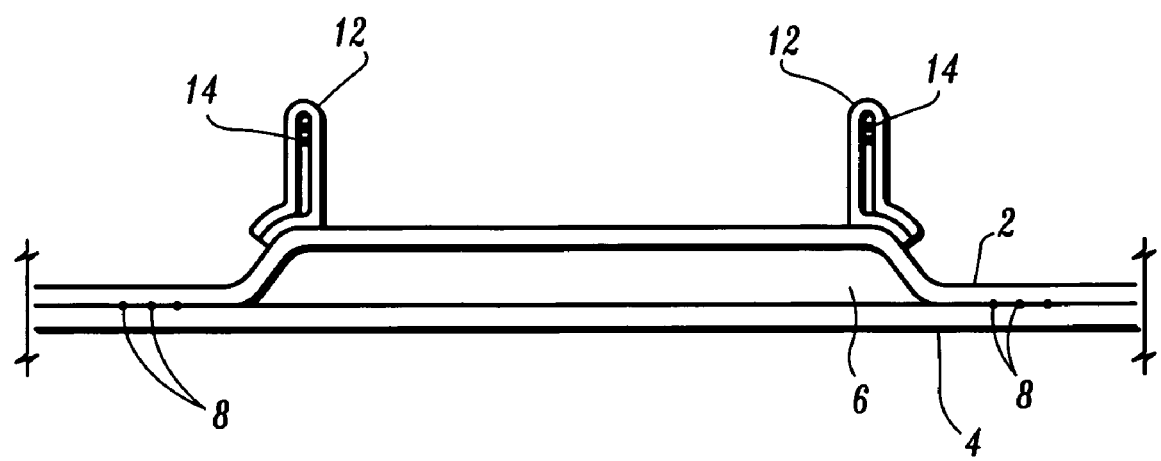
FIG. 4 is a partial side view of the absorbent article according to the present disclosure.

Referring to FIGS. 3 and 2, another advantage provided by the present invention is that the large stretch fastener 32 allows the chassis of diaper 10 to be smaller than in prior art diapers. For example, although the length L of diaper 10 is about the same as the prior art diaper in FIG. 2, the overall width W of diaper 10 in FIG. 3 is less. The reduction in width W occurs along the distal ear portions 38, 46 of diaper 10 (since the core and leg gather section widths remain constant with the particular size of the diaper). This reduction in material provides for a more economical diaper.

Figure 7:
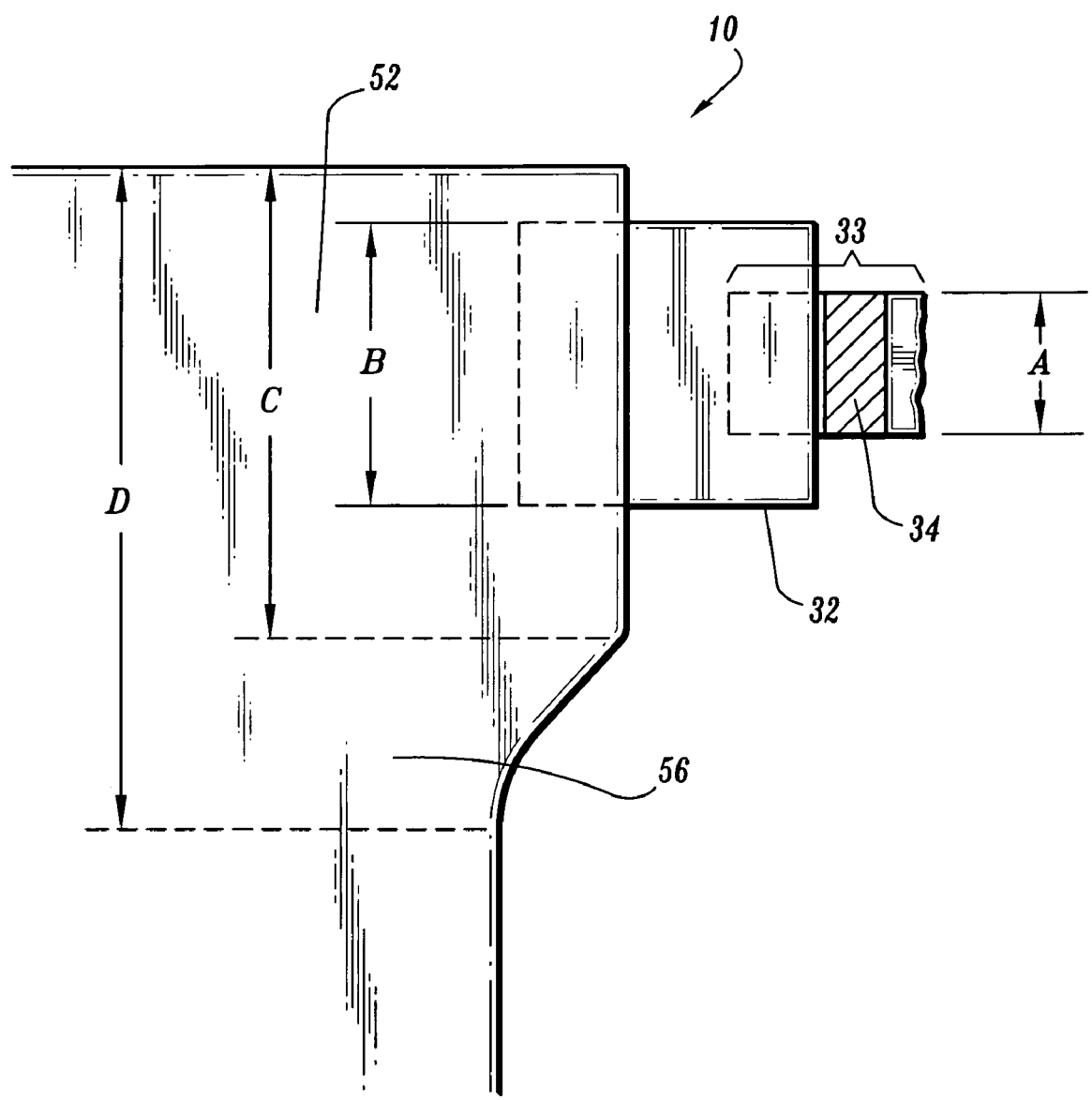
FIG. 7 is a partial plan view of the absorbent article according to the present disclosure.

As more specifically illustrated in FIG. 7, the length A of closure tab 33 is generally between 25 and 45 millimeters and preferably 34 mm. The length B of fastener 32 is generally between 50 and 90 mm and preferably 70 mm. The length C of a fastener attachment area 52 is generally between 95 and 125 mm and preferably 115 mm. The length D of the combined fastener attachment area 52 and the curve of the leg cut out portion 56 is generally between 165 and 195 mm and preferably 185 mm. Length C is between 20-25% and preferably 23% of the length L of the diaper 10. Length D is between 35-40% and preferably 37% of the length L of the diaper 10. Length A is between 45-55% and preferably 50% of length B. Length B is between 55-65% and preferably 60% of length C. Length B is between 17-21% and preferably 19% of length D. Length C is between 55-65% and preferably 60% of length D.

Figure 8:
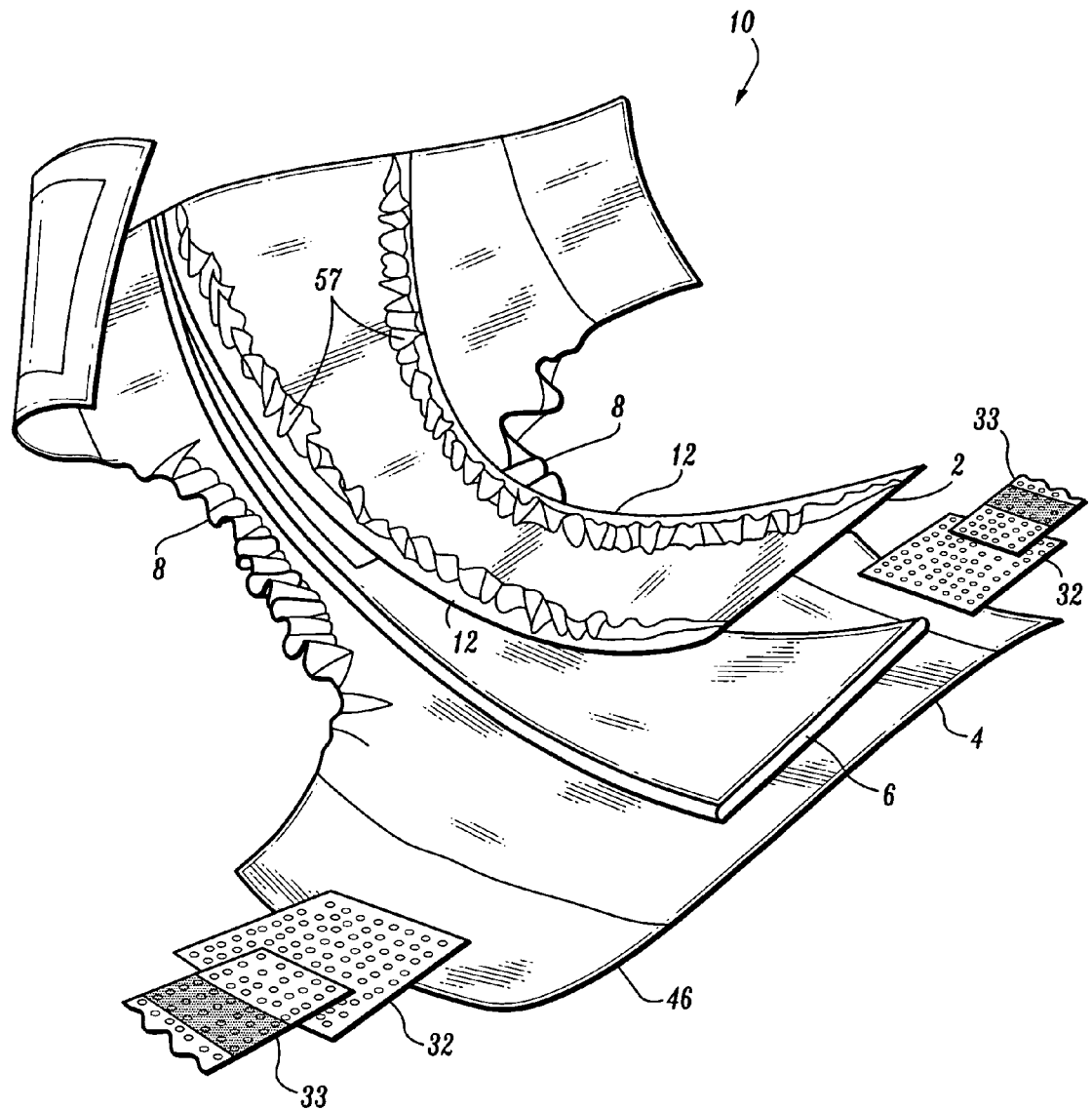
FIG. 8 is an exploded perspective view of the absorbent article according to the present disclosure.

With reference to FIGS. 3 and 8, a pair of elasticized inner leg gathers ("ILG") 12 are provided on opposing sides of core 6. Each ILG 12 extends longitudinally and is disposed with topsheet 2. More specifically, ILG 12 is tacked down to topsheet 2 along a lateral zone 54, and along a back tackdown zone 25 and a front tackdown zone 29. Back tackdown zone 25 extends from edge 58 of diaper 10 and front tackdown zone 29 extends from edge 50 thereof.

ILG 12 includes a plurality of, preferably two, lengthwise elastic members ("elastics") 14 for distributing elastic contractile forces along the ILG 12. Elastics 14, preferably in a stretched state, are adhered to ILG 12 and extend therealong between back 25 and front 29 tackdown zones. Elastics 14 may or may not extend into the back 25 and front 29 tackdown zones. In this stretched position, elastics members 14 form gathered sections 57 that rise or gather up above topsheet 2 to bar leakage of body exudates from diaper 10. Tackdown zones 25 and 29 exclude gathered sections 57 since elastics 14 are not adhesively attached in those zones 25 and 29.

The present disclosure provides an ILG 12 with improved and increased waste containment, as compared with prior art ILG's. Such improvement is achieved at least in part by providing:

1) Tackdown zones 25 and 29 having a total, combined tackdown length that is between 10-25%, preferably 20%, of the length L of diaper 10, as compared to prior art ILG's that disclose tackdown lengths between 30 to 40% of a diaper length L;

2) Elastics 14 having an adhesive bonded length that is between 75-95%, preferably 76%, of the length L of diaper 10. This is compared with prior art ILG elastics that disclose adhesively bonded lengths of between 54-70% of a diaper length; and 3) A ratio of elastic gathered length-to-tackdown zone length (i.e., elastics 14 to tackdown zones 25, 29) that is between 2.5 to 1 and 4.5 to 1, preferably 3.75 to 1, as compared with prior art ILG's that disclose elastic gathered length-to-tackdown zone length ratios between 1.34 to 1 and 2.23 to 1.

The shorter tackdown zones 25, 29 and longer elastics 14 and gathered sections 57 enable ILG 12 to gather up more readily and to have an enhanced gasketing or pocketing effect around the legs of the wearer, as compared with prior art ILG's. Consequently, the leakage of body exudates from diaper 10 is greatly minimized.

EXAMPLE 1

A comparison was performed on various absorbent article products in order to compare the various dimensions and length ratios of the products. The results of this comparison are set forth in TABLE 1 below. An absorbent article product made in accordance with Example 1 of the present disclosure has shorter tackdown zones, longer elastics and gathers, and a greater elastic length-to-tackdown zone length ratio, as compared with the other products tested which include Tyco Snoopy Supreme™ and Tyco UltraFits™ commercially available from TYCO Healthcare Retail Group, Pampers Waddle-Free™ and Pampers Custom Fit™ commercially available from The Procter & Gamble Company, and Huggies Ultratrim™ and Huggies Supremes™ commercially available from the Kimberly-Clark Corporation.

TABLE 1

| | Product Length | Core Length | F/Tack Length | B/Tack Length | Elastic Tacked Length | Elastic Tacked Length as % of Product Length | F/Tack + B/Tack as % of Product Length | Elastic length-to-Tack length Ratio |
| --- | --- | --- | --- | --- | --- | --- | --- | --- |
| Example 1; Present Disclosure | 495 | 425 | 50 | 50 | 375 | 76% | 20% | 3.75 |
| Prior Supreme | 488 | 381 | 57 | 103 | 286 | 59% | 33% | 1.79 |
| UltraFits | 488 | 381 | 57 | 103 | 286 | 59% | 33% | 1.79 |
| Pampers Waddle-Free | 494 | 410 | 65 | 90 | 345 | 70% | 31% | 2.23 |
| Pampers Custom Fit | 490 | 425 | 95 | 55 | 320 | 65% | 31% | 2.13 |
| Huggies Ultratrim | 470 | 375 | 120 | 75 | 290 | 62% | 41% | 1.49 |
| Huggies Supremes | 475 | 390 | 60 | 130 | 255 | 54% | 40% | 1.34 |

Figure 9:
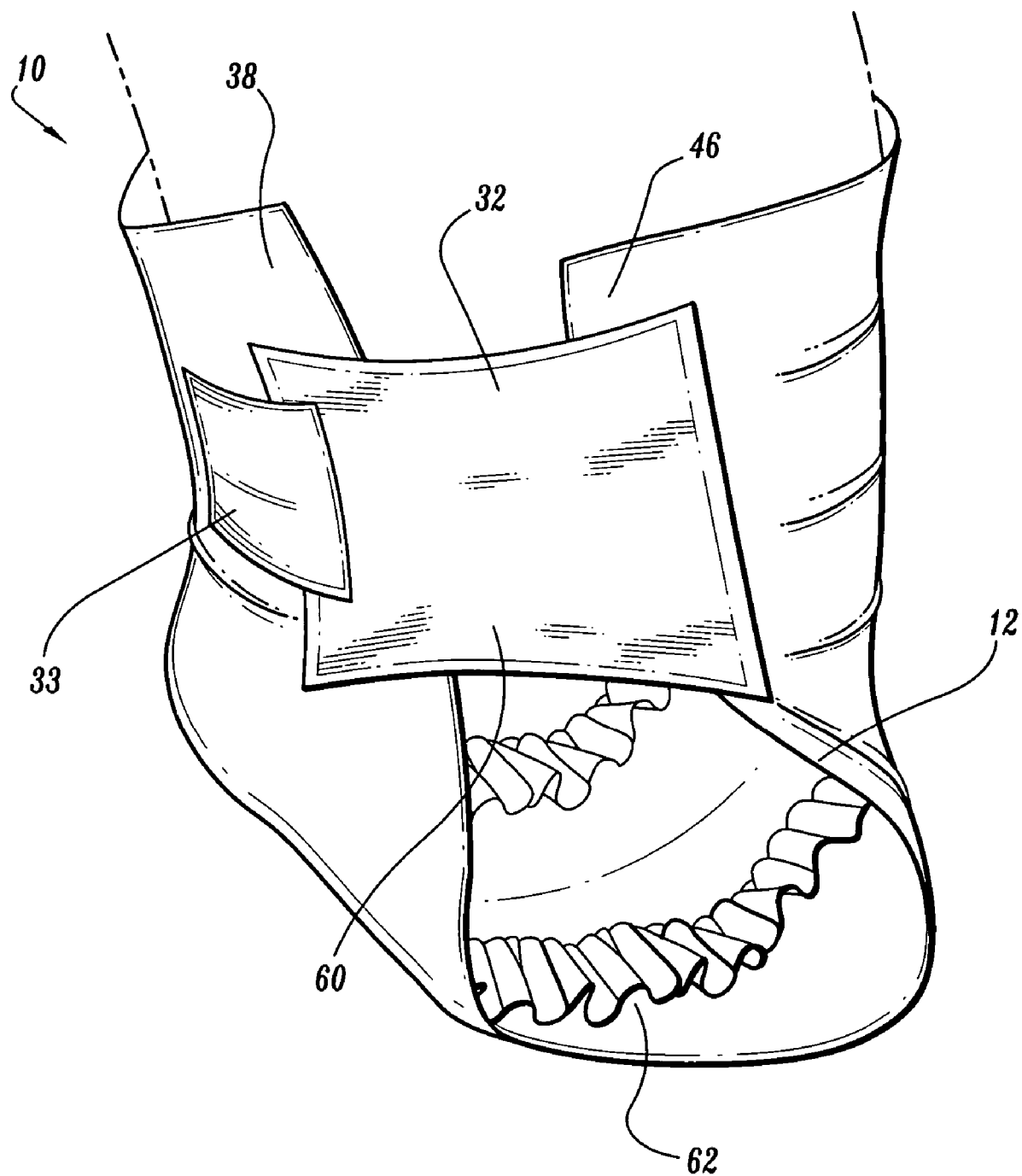
FIG. 9 is a perspective view of the absorbent article according to the present disclosure.

As illustrated in FIG. 9, the above described leg gathers 12 cooperate with the large, rectangular stretch fastener 32 to enhance the gasketing of the wearer's legs. That is, inner leg gathers 12 and fasteners 32 are sized in relationship to each other to enable a complete encircling of each leg to form a better leg gasket for waste containment and fit (i.e., keeping the diaper in place). More specifically, fastener 32 engages the upper thigh/hip of the wearer, and leg gather 12 engages the inner leg/crotch thereof. In this way, fastener 32 and leg gather 12 cooperate to form a more complete unitary gasket having upper (outer portion of wearer's leg, i.e., thigh area) 60 and lower (inner portion of wearer's leg, i.e., crotch area) 62 leg gasket portions about the leg, so that there is less room for exudates to escape.

In contrast, the prior art diaper shown in FIG. 1 includes a smaller fastener that is the only means for holding the diaper up (in place) and for providing coverage on the sides. Thus, the smaller fastener and leg gather fail to encircle the leg completely, resulting in poorer waste containment and fit. This failure is particularly pronounced when the side panels 38, 46 shift in response to the movement of an active infant wearer. On the other hand with diaper 10 of the present invention having large rectangular fastener 32, the side panels 38, 46 have better coverage because of the larger size and square shape of fastener 32.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A diaper comprising:
   a backsheet, a topsheet, and an absorbent core disposed therebetween, the diaper extending from a front end to a back end along a longitudinal length of the diaper;
   at least one longitudinally extending, inner leg gather disposed with the topsheet and extending over and overlapping the absorbent core along the entire length of the absorbent core, the inner leg gather including at least one elastic member for distributing elastic contractile forces and having a length between 75 and 95 percent of the length of the diaper; and
   the inner leg gather being joined to the topsheet along a front tackdown zone and a back tackdown zone, wherein the front and back tackdown zones have a combined length between 10 and 25 percent of the length of the diaper.

2. A diaper according to claim 1, wherein a portion of the at least one elastic member forms gathered sections along the inner leg gather.

3. A diaper according to claim 2, wherein the front and back tackdown zones do not include the gathered sections.

4. A diaper according to claim 1, wherein the front tackdown zone extends from an edge of the first end and the back tackdown zone extends from an edge of the second end.

5. A diaper according to claim 1, further comprising a fastener attached to the back end and being engageable with the front end for disposing the diaper about a subject, the fastener being configured to engage an upper portion of a leg of the subject to facilitate containment about the upper portion of the leg of the subject.

6. A diaper as recited in claim 5, wherein at least a portion of the fastener is extensible in a single lengthwise direction.

7. A diaper as recited in claim 5, wherein the fastener has a rectangular configuration.

8. A diaper as recited in claim 5, wherein the fastener has a square configuration.

9. A diaper as recited in claim 5, wherein the fastener has a side dimension greater than or equal to 50 mm.

10. A diaper as recited in claim 5, wherein the leg gather engages the leg to facilitate containment about a lower portion of the leg of the subject.

11. An absorbent article as recited in claim 5, wherein the fastener and the leg gather cooperate to form a gasket about the leg of the subject.

12. An absorbent article as recited in claim 5, wherein the fastener includes a closure tab for engaging the front end of the diaper.

13. A diaper comprising:
    a backsheet, a topsheet, and an absorbent core disposed therebetween, the diaper extending from a first end to a second end along a longitudinal length of the diaper;
    at least one longitudinally extending, inner leg gather disposed with the topsheet and extending over and overlapping the absorbent core along the entire length of the absorbent core, the inner leg gather including at least one elastic member for distributing elastic contractile forces;
    the inner leg gather being joined to the topsheet along at least one tackdown portion; and wherein a ratio of a length of the elastic member to a length of the tackdown portion is between 2.5 to 1 and 4.5 to 1.

14. A diaper according to claim 13, wherein a portion of the elastic member forms gathered sections along the inner leg gather.

15. A diaper according to claim 13, wherein the tackdown portion does not include the gathered sections.

* * * * *